United States Patent
Lee et al.

(10) Patent No.: US 11,104,927 B2
(45) Date of Patent: Aug. 31, 2021

(54) RECOMBINANT MICROORGANISM FOR PRODUCING CROCIN AND METHOD FOR PRODUCING CROCIN USING THE SAME

(71) Applicant: AJOU UNIVERSITY INDUSTRY-ACADEMIC COOPERATION FOUNDATION, Suwon-si (KR)

(72) Inventors: Pyung Cheon Lee, Yongin-si (KR); Jun Ho Lee, Hwaseong-si (KR)

(73) Assignee: AJOU UNIVERSITY INDUSTRY-ACADEMIC COOPERATION FOUNDATION, Suwon-si (KR)

( * ) Notice: Subject to any disclaimer, the term of this patent is extended or adjusted under 35 U.S.C. 154(b) by 0 days.

(21) Appl. No.: 16/704,274

(22) Filed: Dec. 5, 2019

(65) Prior Publication Data
US 2020/0190547 A1 Jun. 18, 2020

(30) Foreign Application Priority Data
Dec. 5, 2018 (KR) .......................... 10-2018-0155530

(51) Int. Cl.
| | |
|---|---|
| *C12P 19/44* | (2006.01) |
| *C12P 17/06* | (2006.01) |
| *C12N 9/02* | (2006.01) |
| *C12N 9/10* | (2006.01) |

(52) U.S. Cl.
CPC ............ *C12P 17/06* (2013.01); *C12N 9/0008* (2013.01); *C12N 9/0069* (2013.01); *C12N 9/1051* (2013.01); *C12P 19/44* (2013.01); *C12Y 102/01003* (2013.01)

(58) Field of Classification Search
None
See application file for complete search history.

(56) References Cited

U.S. PATENT DOCUMENTS

2017/0067063 A1* 3/2017 Kumar ................. C12N 9/0069

OTHER PUBLICATIONS

F. Chai et al. "Heterologous biosynthesis and manipulation of crocetin in *Saccharomyces cerevisiae*", Microbial Cell Factories 16(1):1-14 (Year: 2017).*
Demurtas et al.; "Candidate Enzymes for Saffron Crocin Biosynthesis Are Localized in Multiple Cellular Components"; Compartmentation of Saffron Crocin Biosynthesis; Plant Physiology (American Society of Plant Biologists); Jul. 2018; vol. 177; pp. 990-1006.
A. Copeland et al; Aldehyde Dehydrogenase [Synechococcus elongatus PCC 7942=FACHB-805]; GenBank ABB56521.1; Submitted: Aug. 8, 2005.

* cited by examiner

*Primary Examiner* — Rebecca E Prouty
(74) *Attorney, Agent, or Firm* — Sughrue Mion, PLLC

(57) ABSTRACT

The present disclosure relates to a recombinant microorganism for producing crocin in which a gene (CCD2) encoding carotenoid cleavage dioxygenase, a gene (aldH) encoding crocetin dialdehyde dehydrogenase and a gene (UDP-glycosyltransftrase, UGT) encoding crocin biosynthesis enzyme are introduced, and a method for producing crocin using the same.
Compared with the conventional method for producing crocin, which is produced in small amounts through a part of plants or callus, the production method using the recombinant microorganism of the present disclosure enables mass production of crocin.

5 Claims, 10 Drawing Sheets
Specification includes a Sequence Listing.

1 : Crocin-5
2 : trans-crocetin
3 : cis-crocetin trans-crocetin cis-crocetin

1 : Crocetin diglucosyl ester (Crocin-3)
2 : Beta-D-glucosyl crocetin (Crocin-5)
3 : trans-crocetin
4 : cis-crocetin

RECOMBINANT MICROORGANISM FOR PRODUCING CROCIN AND METHOD FOR PRODUCING CROCIN USING THE SAME

CROSS-REFERENCE TO RELATED APPLICATIONS

This application is based on and claims priority from Korean Patent Application No. 10-2018-0155530, filed on Dec. 5, 2018, with the Korean Intellectual Property Office, the disclosure of which is incorporated herein in its entirety by reference.

TECHNICAL FIELD

The present disclosure relates to a recombinant microorganism for producing crocin, in which a gene (CCD2) encoding carotenoid cleavage enzyme (carotenoid cleavage dioxygenase), a gene (aldH) encoding crocetin biosynthesis enzyme (crocetin dialdehyde dehydrogenase) and a gene (UGT) encoding crocin biosynthesis enzyme (UDP-glycosyltransferase) are introduced into the recombinant microorganism, and a method for producing crocin using the same.

BACKGROUND

Crocin is a yellow pigment contained in the fruit of crocuses and gardenia. Gardenia fruit is composed of ingredients such as α-crocin, β-sitosterol, mannitol, nonacoic acid, etc. Among them, crocin, a glycoside of crocetin to which gentiobiose is bound, is a yellow pigment ingredient. Crocin belongs to carotenoids. A carotenoid pigment is a carboxylic acid hydrocarbon compound, and is mostly fat-soluble, but crocin is a water-soluble pigment. The uses of such crocin have been reported to have the excellent performance of anticancer agents, antioxidants, antihypertensives, antithrombicides and antidepressants, and have great potential in the fields of medicine and food.

As a method for producing crocin, a method for producing crocin in a small amount mainly from the extraction of a part of plants or callus has been used. Specifically, the *gardenia* fruit is crushed and soaked in water and then boiled for about 1 hour, and then the extract is filtered. The same process is repeated three times to obtain extracts and concentrate the extract, thereby obtaining crocin. However, such a process for producing crocin has the disadvantage that crocetin may be generated during the production process, and the production yield is not high.

In addition, there has recently been an increasing interest in the production of microorganisms of crocetin, and there are some literatures showing the feasibility of microorganism biosynthesis of crocetin and examples of its production. However, a specific method for producing crocin, particularly a method for producing crocin using recombinant microorganisms, has not been disclosed.

Against this background, the present inventors have advanced the MEP metabolic pathway (non-mevalonate pathway) and zeaxanthin biosynthetic metabolic pathway, which are precursors of crocin, for the purpose of developing a production method capable of mass production of crocin, and produced a recombinant microorganism for producing crocin in which a gene (CCD2) encoding carotenoid cleavage enzyme (carotenoid cleavage dioxygenase), a gene (aldH) encoding crocetin biosynthesis enzyme (crocetin dialdehyde dehydrogenase) and a gene (UGT) encoding crocin biosynthesis enzyme (UDP-glycosyltransferase) are introduced. In addition, the present inventors confirmed that the mass production of crocin is possible by using the same and completed the present disclosure.

SUMMARY

One object of the present disclosure is to provide a recombinant microorganism for producing crocin in which a gene (CCD2) encoding carotenoid cleavage enzyme (carotenoid cleavage dioxygenase), a gene (aldH) encoding crocetin biosynthesis enzyme (crocetin dialdehyde dehydrogenase) and a gene (UGT) encoding crocin biosynthesis enzyme (UDP-glycosyltransferase) are introduced.

Another object of the present disclosure is to provide a method for producing crocin including culturing the recombinant microorganism.

Each description and embodiment disclosed in the present disclosure may be applied to each other description and embodiment. That is, all combinations of the various elements disclosed in the present disclosure fall within the scope of the present disclosure. In addition, the scope of the present disclosure is not to be limited by the specific description described below.

As one aspect for achieving the above object, the present disclosure provides a recombinant microorganism for producing crocin in which a gene (CCD2) encoding carotenoid cleavage enzyme (carotenoid cleavage dioxygenase), a gene (aldH) encoding crocetin biosynthesis enzyme (crocetin dialdehyde dehydrogenase) and a gene (UGT) encoding crocin biosynthesis enzyme (UDP-glycosyltransferase) are introduced.

As used herein, the term "cartotenoid cleavage enzyme (carotenoid cleavage dioxygenase)" is a protein belonging to a non-heme iron II dependent enzyme, and catalyzes the selective oxidative cleavage of carotenoids to produce apocarotenoids. The carotenoid cleavage enzyme of the present disclosure may be used to produce crocetin dialdehyde based on zeaxanthin.

A gene (CCD2) encoding the carotenoid cleavage enzyme may be derived from a plant of the genus *Crocus*. Specifically, it may be derived from *Crocus sativus*, but is not limited thereto.

In a specific embodiment of the present disclosure, a recombinant microorganism was prepared by introducing a carotenoid cleavage enzyme (CsCCD2) derived from *Crocus sativus* into a ZEA-1 strain that has an advanced MEP metabolic pathway and a zeaxanthin biosynthesis pathway. By culturing the microorganism, it was confirmed that crocetin dialdehyde could be biosynthesized (FIGS. 2A and 2B).

As used herein, the term "crocetin biosynthesis enzyme (crocetin dialdehyde dehydrogenase)" is an enzyme that converts crocetin dialdehyde produced from zeaxanthin by the carotenoid cleavage enzyme to crocetin.

A gene (aldH) encoding crocetin biosynthesis enzyme may be derived from the genus *Cinechococcus*. Specifically, it may be derived from *Synechococcus elongatus*, but is not limited thereto.

In a specific embodiment of the present disclosure, a recombinant microorganism was prepared by introducing a carotenoid cleavage enzyme (CsCCD2) derived from *Crocus sativus* and crocetin biosynthesis enzyme (aldH_7942) derived from *Synechococcus elongatus* into a ZEA-1 strain that has an advanced MEP metabolic pathway and a zeaxanthin biosynthesis pathway. By culturing the microorganism, it was confirmed that crocetin could be biosynthesized with high efficiency (FIGS. 3A-3C and 4A-4B).

As used herein, the term "crocin biosynthesis enzyme (UDP-glycosyltransferase)" catalyzes the transfer of the glucuronic acid component of UDP-glucuronic acid to small hydrophobic molecules, which is cytosolic glycosyltransferase (EC 2.4.1.17). The crocin biosynthesis enzyme (UDP-glycosyltransferase, UGT) of the present disclosure may produce a glucuronidation reaction from the crocetin produced by the crocetin biosynthesis enzyme to biosynthesize crocin.

A gene (UGT) encoding the crocin biosynthesis enzyme (UDP-glycosyltransferase) may be derived from a plant of the genus *Gardenia*. Specifically, it may be derived from *Gardenia jasminoides*, but is not limited thereto.

In a specific embodiment of the present disclosure, a recombinant microorganism was prepared by introducing a carotenoid cleavage enzyme (CsCCD2) derived from *Crocus sativus*, crocetin biosynthesis enzyme (aldH_7942) derived from *Synechococcus elongatus*, and crocin biosynthesis enzyme (UDP-glycosyltransferase) (UGT-1) derived from *Gardenia jasminoides* into a ZEA-1 strain that has an advanced MEP metabolic pathway and a zeaxanthin biosynthesis pathway. By culturing the microorganism, it was confirmed that crocetin could be biosynthesized with high efficiency (FIGS. 5A-5B).

In particular, in one specific embodiment of the present disclosure, it was confirmed that the efficiency of crocetin and crocin biosynthesis may vary significantly depending on the origin of the introduced gene (Table 3).

As used herein, the term "recombinant microorganism" refers to a strain transformed by introducing or activating genes encoding the carotenoid cleavage enzyme, crocetin biosynthesis enzyme and crocin biosynthesis enzyme.

The recombinant microorganism may be a recombinant microorganism having introduced a carotenoid cleavage enzyme consisting of an amino acid sequence represented by SEQ ID NO: 1, a crocetin biosynthesis enzyme consisting of an amino acid sequence represented by SEQ ID NO: 2, and a crocin biosynthesis enzyme consisting of an amino acid sequence represented by SEQ ID NO: 3, but is not limited thereto.

Each of the carotenoid cleavage enzyme, crocetin biosynthesis enzyme and crocin biosynthesis enzyme is an amino acid sequence represented by SEQ ID NOS: 1 to 3 showing a homology of 70% or more, specifically 80% or more, more specifically 90% or more, even more specifically 95% or more, and most specifically 99% or more, and may be included without limitation as long as each of them is a protein having substantially each enzyme activity.

As used herein, the term "homology" refers to a degree of agreement with a given amino acid sequence and may be expressed as a percentage. In this specification, homologous sequences that have the same or similar activities as a given amino acid sequence are denoted as "% homology". For example, it was confirmed by comparing sequences using standard software that calculates parameters such as score, identity and similarity, in particular BLAST 2.0, or hybridization experiments used under defined stringent conditions. It may be determined by methods well known to those skilled in the art.

The recombinant microorganism may use a vector to remove or introduce a gene. The vector is not limited thereto, but is not particularly limited as long as the carotenoid cleavage enzyme, crocetin biosynthesis enzyme and crocin biosynthesis enzyme genes can be introduced into the host microorganism, and may be produced using any vector known in the pertinent field. Examples of commonly used vectors include natural or recombinant plasmids, cosmids, viruses and bacteriophages. For example, pWE15, M13, MBL3, MBL4, IXII, ASHII, APII, t10, t11, Charon4A, Charon21A, etc. may be used as a phage vector or cosmid vector, and pBR-based, pUC-based, pBluescriptII-based, pGEM-based, pTZ-based, pCL-based, pET-based, etc. may be used as a plasmid vector. The vector usable in the present disclosure is not particularly limited and known expression vectors may be used.

The recombinant microorganism is not particularly limited thereto, but may be a microorganism of the genus *Saccharomyces* or *Escherichia*. Specifically, microorganisms of the genus *Saccharomyces* may be *Saccharomyces cerevisiae*, and microorganisms of the genus *Escherichia* may be *Escherichia coli*.

In another aspect of the present disclosure, there is provided a method for producing crocin including culturing the recombinant microorganism.

In this case, the recombinant microorganism is as described above.

As used herein, the term "culture" means growing a desired cell or tissue under artificially controllable environmental conditions. Artificially controlled environmental conditions typically include nutrients, temperature, osmotic pressure, pH, gas composition, light, etc., but the medium has a direct effect thereon, in which the medium is largely divided into a liquid medium and a solid medium.

The step may further include recovering crocin from the cultured microorganism or its culture.

The crocin recovery step may be performed by a suitable method known in the pertinent field depending on the culture method. Specifically, known methods of recovering crocin are not particularly limited thereto, but methods such as centrifugation, filtration, extraction, spraying, drying, evaporation, precipitation, crystallization, electrophoresis, fractional dissolution (e.g., ammonium sulfate precipitation), chromatography (e.g., HPLC, ion exchange, affinity, hydrophobicity and size exclusion) may be used, but are not limited thereto.

Compared with the conventional method for producing crocin, which is produced in small amounts through a part of plants or callus, the production method using the recombinant microorganism of the present disclosure enables mass production of crocin.

DETAILED DESCRIPTION

Hereinafter, the present disclosure will be described in more detail with reference to the following examples. However, these examples are for illustrative purposes only and the scope of the present disclosure is not limited only to these examples.

<Example 1> Preparation of Recombinant Microorganisms for Crocin Production 1-1. Advancement of MEP Metabolic Pathway and Zeaxanthin Biosynthetic Pathway In order to proceed with the biosynthesis of crocetin, which is a precursor of crocin in *E. coli*, it is necessary to advance the MEP metabolic pathway and the zeaxanthin biosynthetic metabolic pathway, which are precursors of crocetin, so it was inserted into the chromosome of *Escherichia coli* K12 MG1655 strain.

Specifically, the advancement of MEP metabolic pathway was progressed in a way such that *E. coli*-derived ispA (geranyl diphosphate/farnesyl diphosphate synthase), idi (isopentenyl-diphosphate A-isomerase), dxs (1-deoxy-D-xylulose-5-phosphate synthase), dxr (1-deoxy-D-xylulose 5-phosphate reductoisomerase) genes were expressed by constitutive expression lac promoters.

Through the above process, the advancement of the zeaxanthin biosynthetic metabolic pathway in the strain with the strengthened MEP metabolic pathway was performed. Specifically, the zeaxanthin biosynthetic metabolic pathway was advanced so that the zeaxanthin synthetic genes CrtE, CrtB, CrtI, CrtY, CrtZ genes derived from *Pantoea agglomerans* were expressed by the systemic expression trc promoter. As a result, ZEA-1 strains which strengthened the MEP metabolic pathway and capable of producing zeaxanthin were obtained.

1-2. Introduction of Genes Related to Crocin Biosynthesis

In order to proceed with the biosynthesis of crocetin dialdehyde to the strain obtained in Example 1-1 above, CsCCD2, which is a gene encoding a carotenoid cleavage dioxygenase derived from *Crocus sativus*, was subjected for gene synthesis by GenScript. After amplification by PCR, cloning was carried out at EcoRI and HindIII sites of pKK223-3 vector. Subsequently, subcloning was carried out at BglII and NotI sites of pSTVM vector.

Subsequently, in order to proceed with the biosynthesis of crocetin, aldH, which is a gene encoding crocin dialdehyde dehydrogenase, was amplified by PCR on chromosomal DNA of *Synechococcus elongatus* PCC 7942, and then cloning was carried out at XbaI and EcoRI sites of pUCM vector. Subsequently, subcloning was carried out at SalI and EcoRI sites of pBBR1MCS-2 vector.

Subsequently, in order to proceed with the biosynthesis of crocin-5, UGT, which is a gene encoding crocin biosynthesis enzyme (UDP-glycosyltransferase) was subjected for gene synthesis by GenScript through the request of the UGT75L6 (UGT-1) of *Gardenia jasminoides*. After amplification by PCR, cloning was carried out at EcoRI and PstI sites of pKK223-3 vector.

Figure 1A:
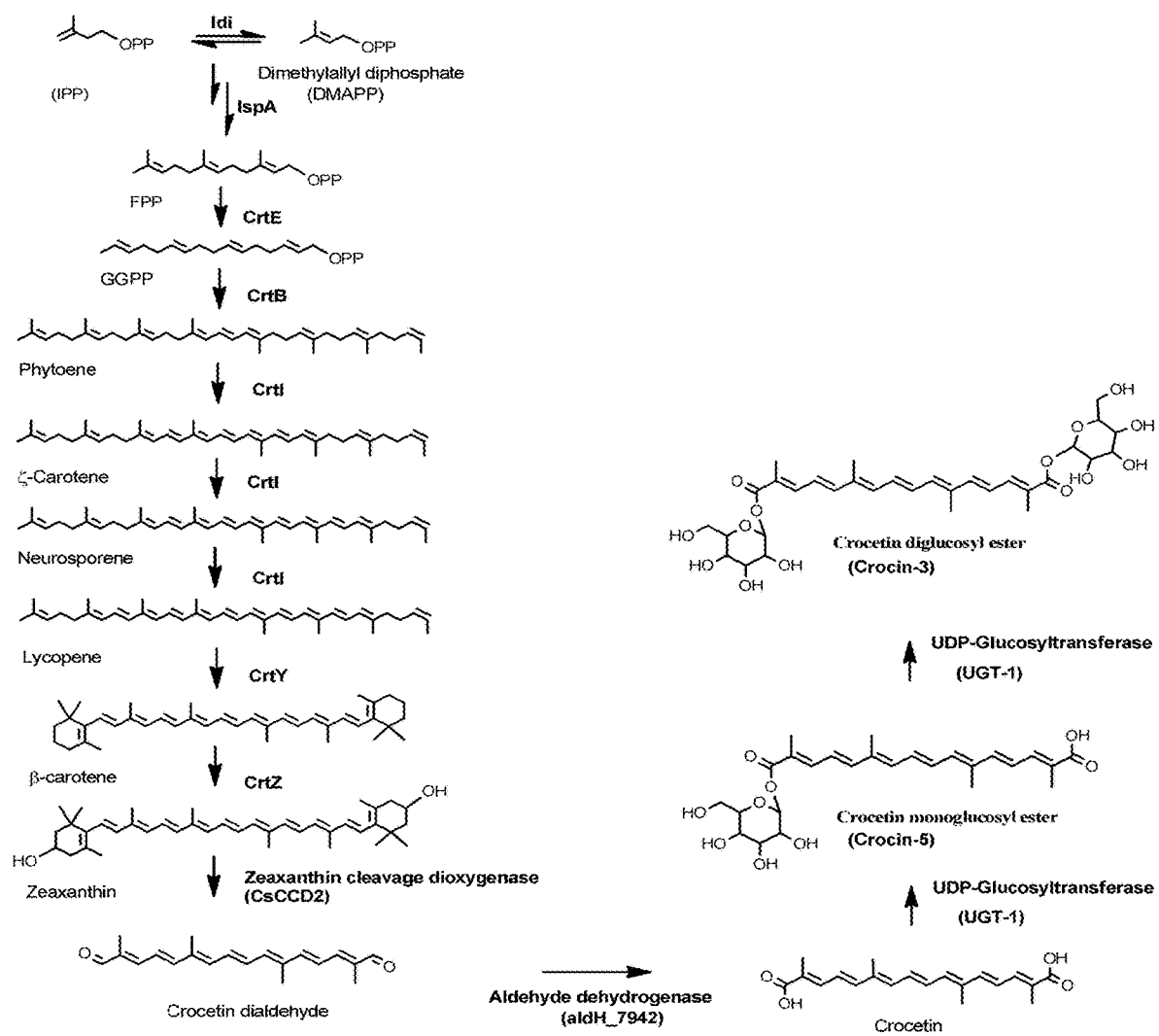
FIGS. 1A and 1B illustrate a schematic diagram of a vector introduced into a strain in which the crocin-5 biosynthetic metabolic pathway constructed in *E. coli* and the MEP metabolic pathway and the zeaxanthin biosynthetic pathway were advanced.
Figure 1B:
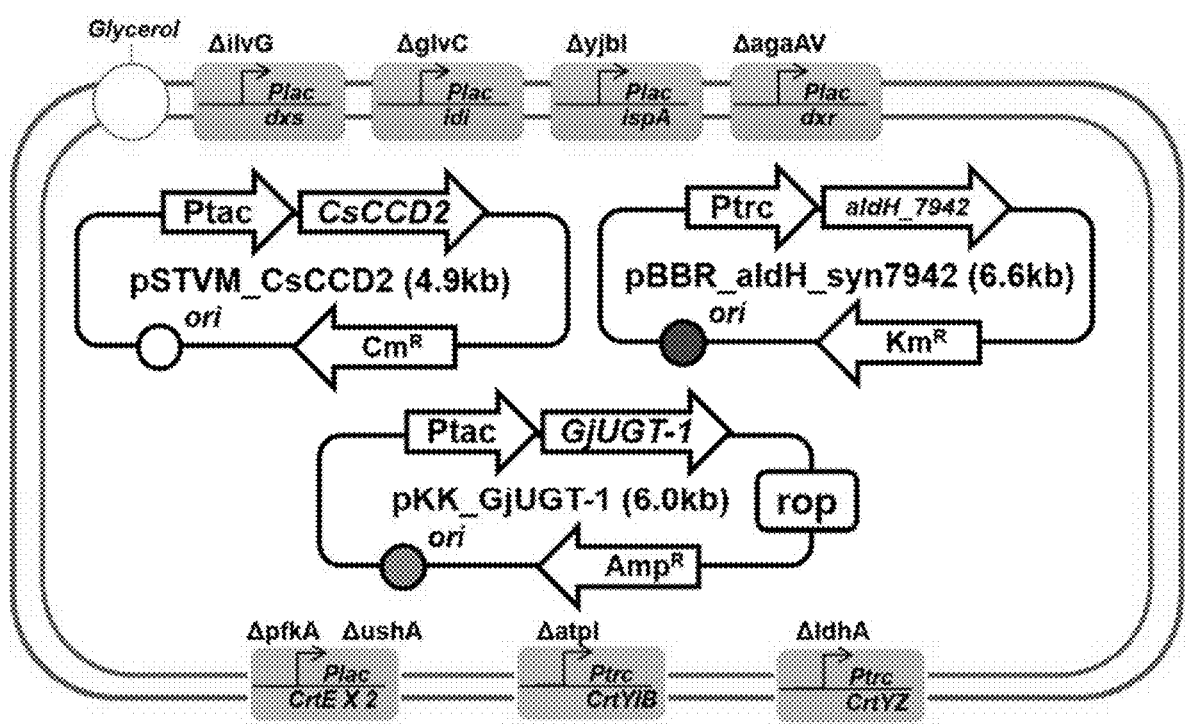

As a result, as can be confirmed from FIGS. 1A and 1B, a recombinant microorganism for producing crocin into which carotenoid cleavage dioxygenase gene (CsCCD2), crocin dialdehyde dehydrogenase gene (aldH_7942) and crocin biosynthesis enzyme (UDP-glycosyltransferase) gene (UGT-1) were introduced was produced.

The microbial strain and the constructed plasmid used in the above process are shown in Table 1 below.

TABLE 1

| Strains and Plasmids | Related characteristics |
| --- | --- |
| Strains | |
| MG1655 | (IlvG rfb-50 rph-1) |
| ZEA-1 | MG1655 (IlvGΔ::PLac-dxs glvC Δ::PLac-idl, yjblΔ::PLac-ispA, agaAV Δ::PLac-dxr, pfkAΔ::PLac-CrtE, atpl Δ::Ptrc-CrtYIB, ldhAΔ::Ptrc-YZ) |
| *Synechococcus elongatus* PCC 7942 | |
| Plasmids | |
| pUCM | Cloning vector modified from pUC19. |
| pKK223-3 | Constitutive lac promoter, $Ap^r$ tac promoter, $Ap^r$ |
| pSTVM | Plasmid vector is reconstructed with a replication origin of pACYC184, $Cm^r$ |
| pKK_CaCCD2 | $Ap^r$, CsCCD2 cloned in EcoR1 and HindIII site of pkk223-3 |
| pSTVM_C₃CCD2 | $Cm^r$, CoCCD2 cloned in BglIII and NotI site of pSTVM |
| pUCM_aldH_7942 | $Ap^r$, aldH cloned in XbaI and EcoRI site of pUCM |
| pBBR_aldH_7942 | $Km^r$, aldH cloned in SalI and EcoRI site of pBBR1MCS2 |
| pKK_UGT-1 | $Ap^r$, CsCCD2 cloned in EcoRI and PstI site of pkk223-3 |

The forward and reverse primers used in the polymerase chain reaction were prepared based on the result of comparing and analyzing the base sequence information of genes encoding enzymes associated with mevalonate biosynthetic pathways in each strain and the information shown in NCBI (National Center for Biotechnology Information, http://www.ncbi.nlm.nih.gov/). The base sequences of the forward and reverse primers used for amplification of each gene are shown in Table 2 below.

TABLE 2

| Genes | Primer Sequences | Enzyme Locations |
| --- | --- | --- |
| CsCCD2 | F: 5'-CGGAATTCATGGCGAACAAAGAAGAGG (SEQ ID NO: 7) | EcoRI |
| | R: 5'-CCCAAGCTTTTAGGTCTCCGCTTGATGC (SEQ ID NO: 8) | HindIII |
| aldH_7942 | F: 5'-GCTCTAGAAGGAGGATTACAAAATGACTGCTGTCGTTCTCC (SEQ ID NO: 9) | XbaI |
| | R: 5'-CGGAATTCCTAGAGCTTGCGGAAGAG (SEQ ID NO: 10) | EcoRI |

TABLE 2-continued

| Genes | Primer Sequences | Enzyme Locations |
|---|---|---|
| sub_CCD2_F | F: 5'-GGAAGATCTGCTGTGCAGGTCGTAAA (SEQ ID NO: 11) | BglII |
| sub_CCD2_R | R: 5'-ATAAGAATGCGGCCGCGAAACGCAAAAAGGCCA (SEQ ID NO: 12) | NotI |
| sub_aldH_7942_F | F: 5'-GTCGACCCGACTGGAAAGCG (SEQ ID NO: 13) | SalI |
| sub_aldH_7942_R | R: 5'-CGGAATTCCTAGAGCTTGCGGAAGAG (SEQ ID NO: 14) | EcoRI |
| UGT-1_F | F: 5'-CGGAATTCATGGTTCAGCAGCGTCACGT (SEQ ID NO: 15) | EcoRI |
| UGT-1_R | R: 5'-AACTGCAGTTAGTTGCTCTCCGCTTGAT (SEQ ID NO: 16) | PotI |

<Example 2> Confirmation of Crocin Production Capacity of Recombinant Microorganisms In order to confirm the crocin production capacity of the strains prepared in Example 1 above, the biosynthesis of crocetin dialdehyde, crocetin and crocin of recombinant microorganisms in which the gene (CsCCD2) encoding the carotenoid cleavage enzyme, the gene (aldH_7942) encoding the crocetin biosynthesis enzyme, and the gene (UGT-1) encoding the crocin biosynthesis enzyme were sequentially introduced were confirmed sequentially.

2-1. Confirmation of Crocetin Dialdehyde Biosynthesis

As explained in Example 1, in order to confirm the biosynthesis of crocetin dialdehyde of the recombinant microorganism transformed with the gene (CsCCD2) encoding the crocetin dialdehyde biosynthesis enzyme into strains into which the MEP metabolic pathway and zeaxanthin biosynthesis pathway were inserted, the incubation was carried out under the following incubation conditions.

Specifically, the recombinant microorganism into which the plasmid of CsCCD2 was introduced was incubated for 48 hours at 250 rpm under aerobic conditions in a 100 ml medium using a 500 ml flask. In the case of the incubation temperature, the incubation was carried out at 30° C., and when OD600 became between 0.7 and 1.0, the temperature was converted into 20° C., and then the incubation was continued. As the medium composition, 50 μg/ml of chloramphenicol and 50 μg/ml of kanamycin were all added to a TB (Terrific broth) medium containing 5 g/L of glycerol as a carbon source.

Figure 2A:
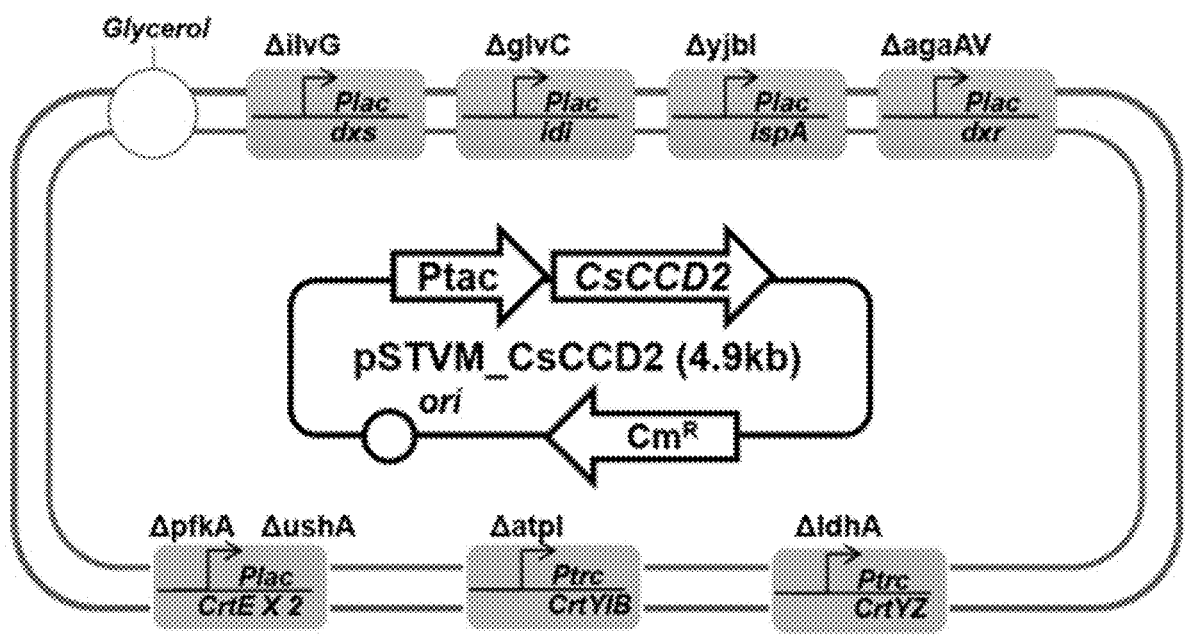
FIGS. 2A and 2B illustrate the results of HPLC analysis of recombinant microorganisms introducing the CsCCD2 gene and the crocetin dialdehyde biosynthetic metabolic pathway constructed in *E. coli* (Peak 1: crocetin dialdehyde).
Figure 2B:
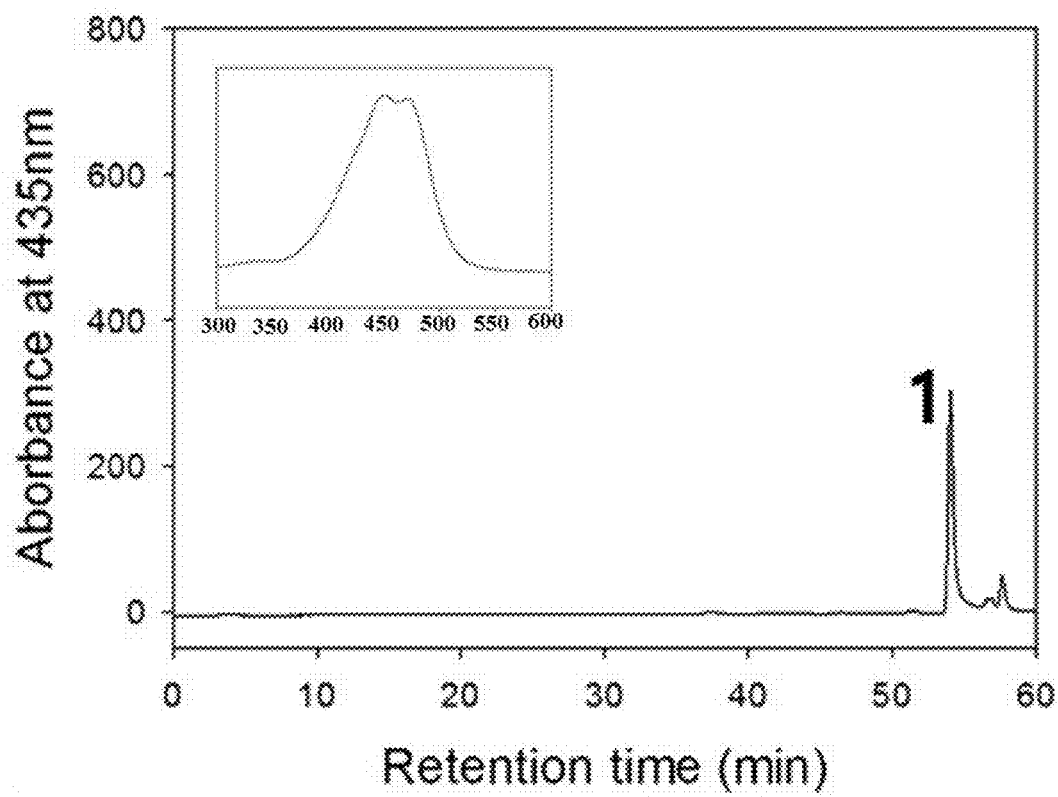

After the incubation process as described above, as a result of analyzing HPLC spectra after extraction, as can be confirmed in FIGS. 2A and 2B, it was confirmed that a peak representing crocetin dialdehyde was observed. Through this, it was possible to confirm the ability to produce crocetin dialdehyde of recombinant microorganisms in which a gene (CsCCD2) encoding the crocetin dialdehyde biosynthesis enzyme was introduced into strains in which the MEP metabolic pathway and zeaxanthin biosynthesis pathway were advanced.

2-2. Confirmation of Crocetin Biosynthesis

As explained in Example 1, in order to confirm the biosynthesis of crocetin of the recombinant microorganism transformed with the gene (CsCCD2) encoding the crocetin dialdehyde biosynthesis enzyme and the gene (aldH_7942) encoding the crocetin biosynthesis enzyme into strains into which the MEP metabolic pathway and zeaxanthin biosynthesis pathway were inserted, the incubation was carried out under the incubation conditions as described in Example 2-1 above.

100 ml of medium incubated for extraction and separation of crocetin was all taken, and centrifuged at 4000 rpm for 20 minutes, and all supernatant was discarded. The obtained cells were washed with 0.9% NaCl solution and centrifuged under the same conditions once again. The cells thus obtained were repeatedly extracted with 5 ml or 10 ml of acetone until the color completely disappeared. The extracted solution was concentrated using a vacuum centrifuge (EZ-2 plus, Genevec), 5 ml of ethyl acetate was added to the concentrated solution, mixed, and 5N NaCl solution was added to separate the solution layer. After separating the upper layer containing the color, it was washed twice with tertiary water to remove the remaining water, and dried completely using a vacuum centrifuge. 100-200 μl of ethyl acetate was added to the completely dried sample, dissolved and used for later analysis.

The structure of crocetin obtained by the culture and extraction methods was confirmed by HPLC retention time, UV-Vis spectrum, and mass spectrometry analysis.

Specifically, HPLC analysis was performed using 10-20 μl of prepared samples, and HPLC spectra were analyzed using A: 100% MeOH (25 mM formic acid) and B: 100% DDW (25 mM formic acid) as mobile phases. As a gradient condition, the solvent A was 50% of up to 50 minutes, the solvent A was 80% of up to 60 minutes, and the solvent A was 100% of up to 80 minutes. Zorbax eclipse XDB-C18 column (4.6×150 mm or 250 mm, 5 μm; Agilent Technology) was analyzed as a fixed phase at a flow rate of 0.8 ml/min. HPLC retention time, absorption spectrum and mass spectrum were compared and analyzed for structural analysis. Mass spectra were monitored for both positive and negative modes using a Varian 1200L LC/MS system, and the atmosphere pressure chemical ionization (APCI) module was used for ionization.

Figure 3A:
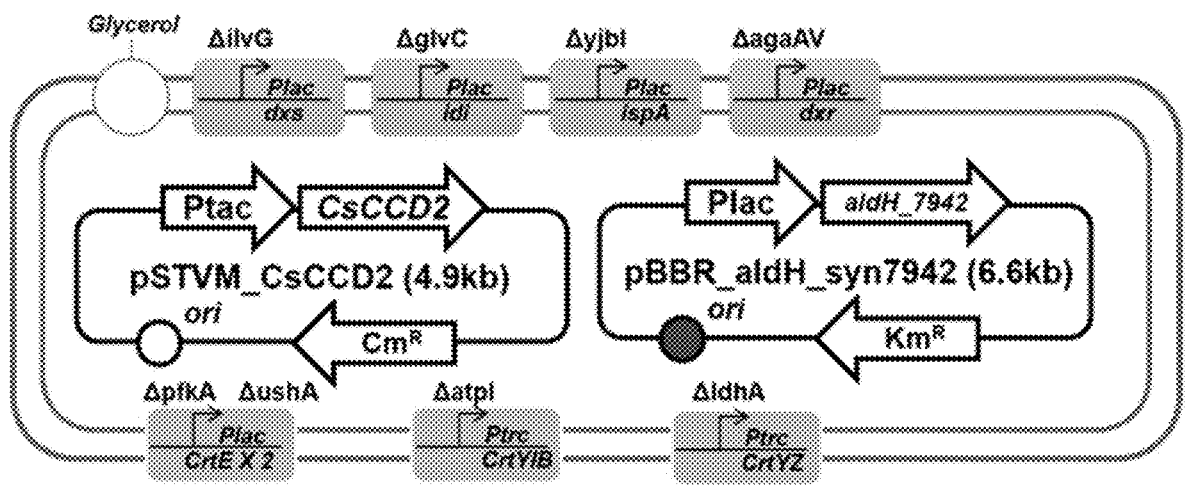
FIGS. 3A-3C illustrate the results of HPLC analysis of recombinant microorganisms introducing the crocetin biosynthetic metabolic pathway constructed in *E. coli*, the CsCCD2 gene, and the aldH 7942 gene.
Figure 3B:
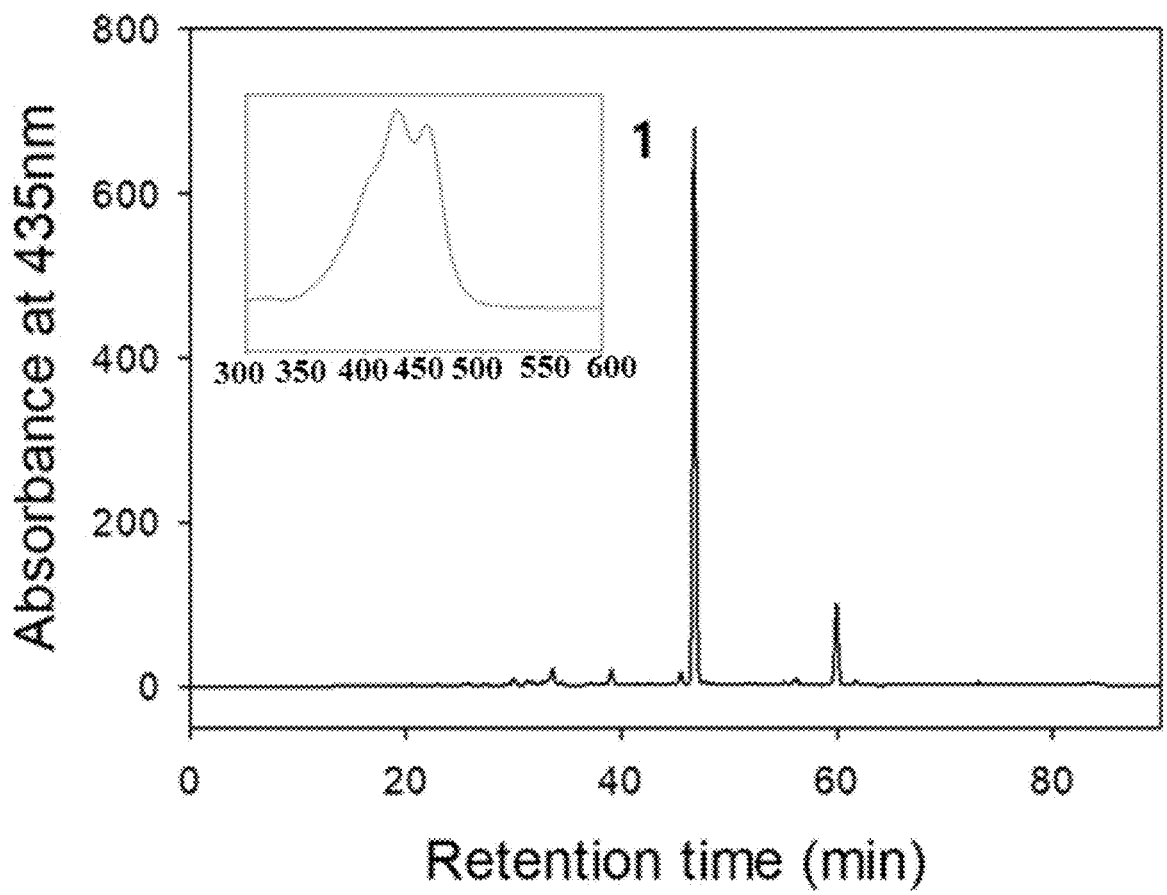
Figure 3C:
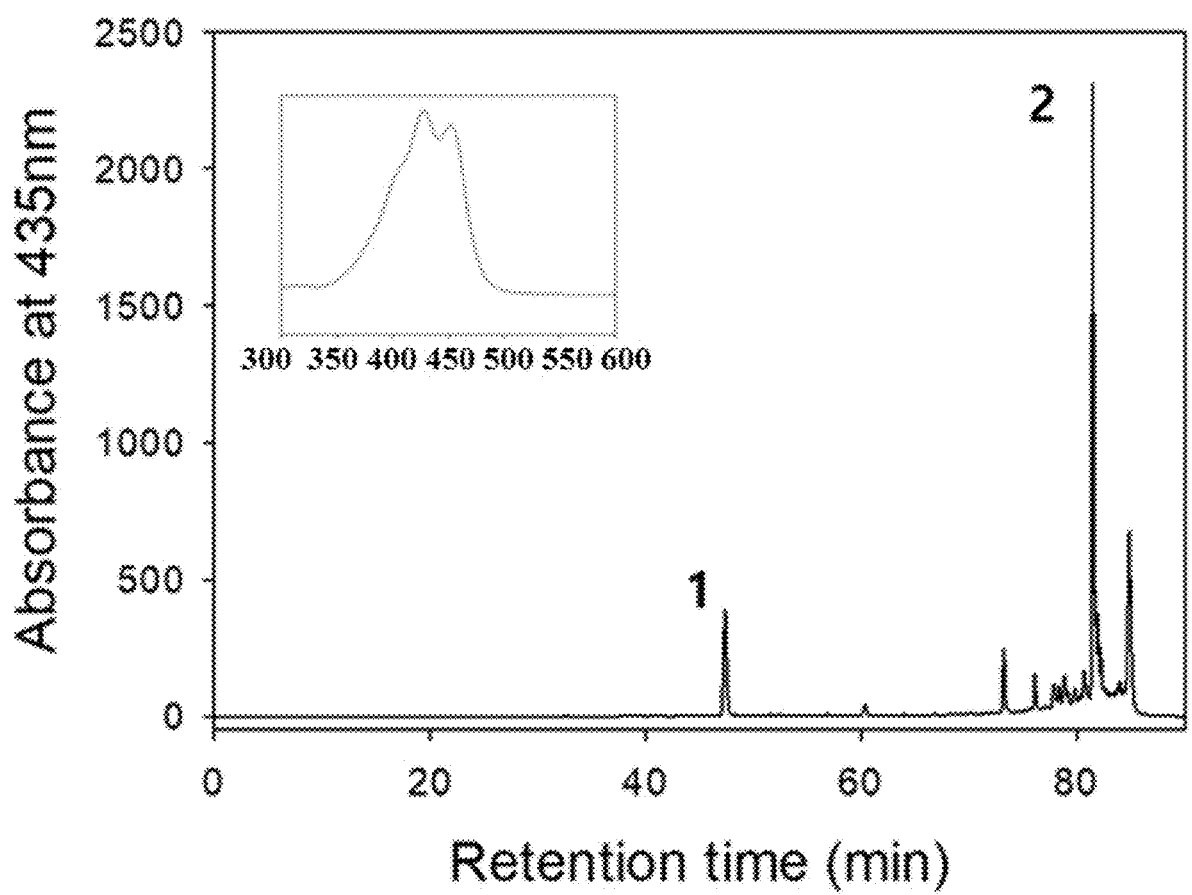
Figure 4A:
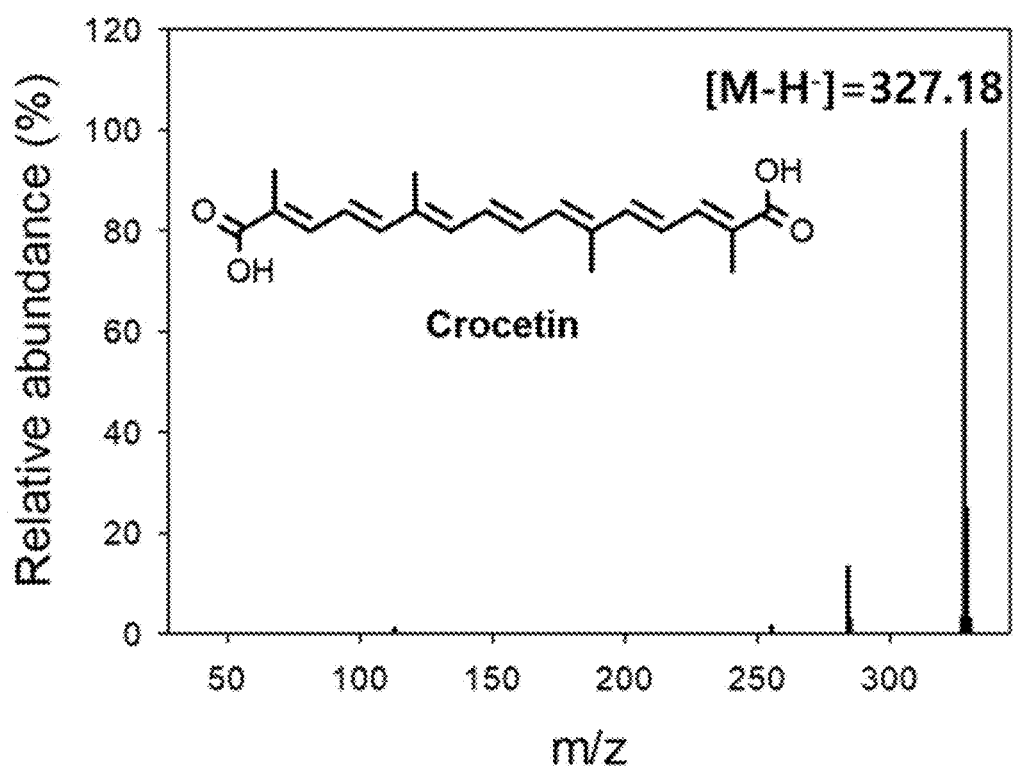
FIGS. 4A and 4B illustrate mass spectral data (FIG. 4A) of crocetin and mass spectral data (FIG. 4B) of crocetin synthesized using a recombinant microorganism into which the CsCCD2 gene and the aldH 7942 gene are introduced.
Figure 4B:
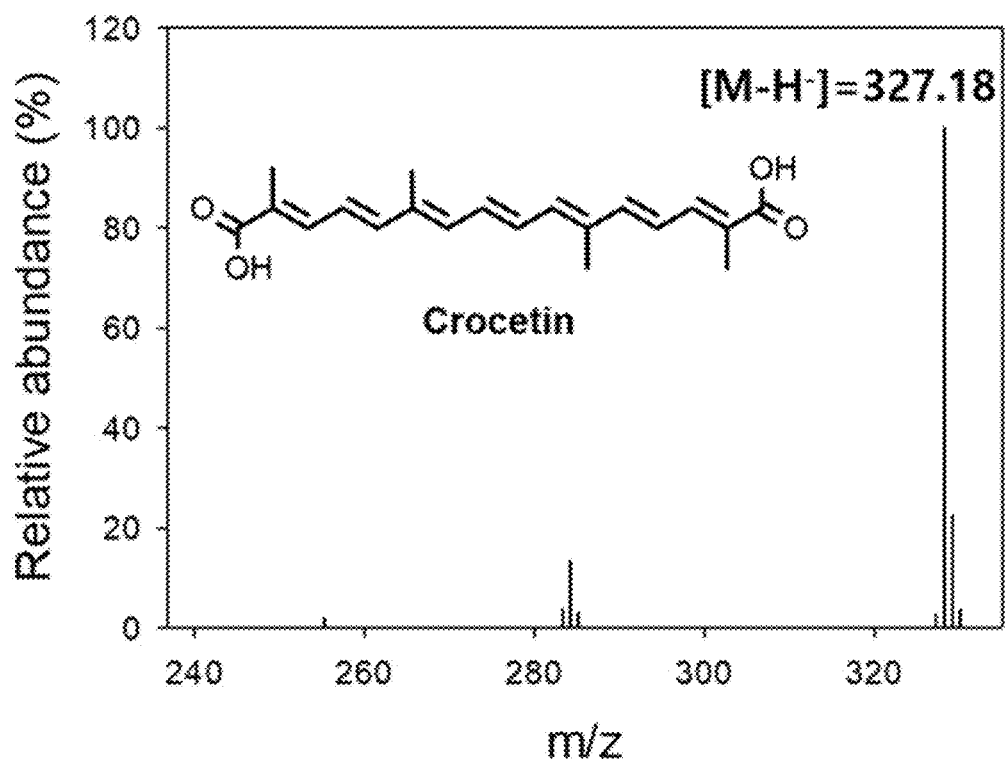

After the incubation process as described above, as a result of analyzing HPLC spectra after extraction, as can be confirmed in FIGS. 3A-3C, it was confirmed that a peak representing crocetin was observed. In addition, as a result of analyzing the mass spectrum, as can be confirmed in FIGS. 4A-4B, it was confirmed that a high concentration of crocetin was produced. Through this, recombinant microorganisms in which a gene (CsCCD2) encoding crocetin dialdehyde biosynthesis enzyme and a gene (aldH_7942) encoding crocetin biosynthesis enzyme were introduced into strains in which the MEP metabolic pathway and zeaxanthin biosynthesis pathway were advanced could produce crocetin with high efficiency.

2-3. Confirmation of Crocin-5 Biosynthesis

As explained in Example 1, in order to confirm the biosynthesis of crocin-5 of the recombinant microorganism transformed with the gene (CsCCD2) encoding the crocetin dialdehyde biosynthesis enzyme, the gene (aldH_7942) encoding the crocetin biosynthesis enzyme, and the gene (UGT-1) encoding the crocin biosynthesis enzyme into strains which the MEP metabolic pathway and zeaxanthin biosynthesis pathway were inserted, the incubation was carried out under the same condition as the incubation condition described in Example 2-1 above. After incubation, crocin was extracted and separated in the same manner as described in Example 2-2 above. The structure of the cultured and extracted crocin was confirmed by HPLC retention time, UV-Vis spectrum, and mass spectrum analysis in the same manner as described in Example 2-2 above.

Figure 5A:
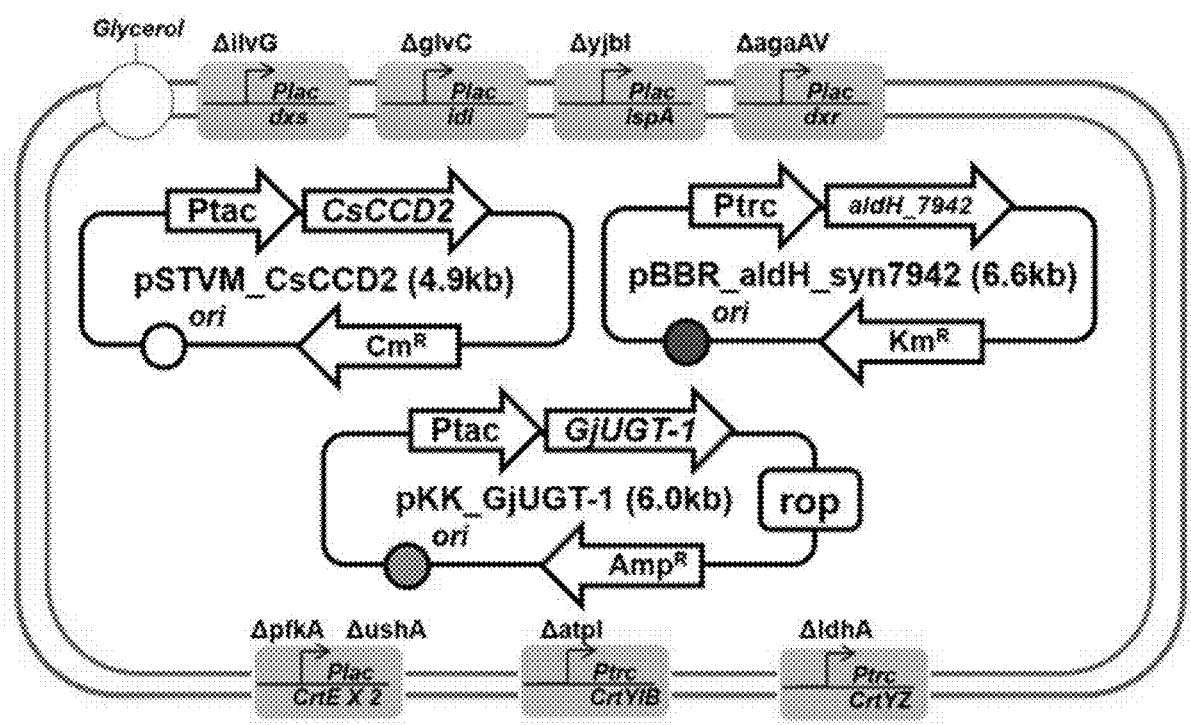
FIGS. 5A and 5B illustrate a schematic diagram of a recombinant microorganism introducing the crocin-5 biosynthetic metabolic pathway constructed in *E. coli*, the CsCCD2 gene, the aldH 7942 gene and the UGT-1 gene (FIG. 5A), and HPLC spectrum and mass spectrum analysis results of crocetin and crocin synthesized using the recombinant microorganism (FIG. 5B).
Figure 5B:
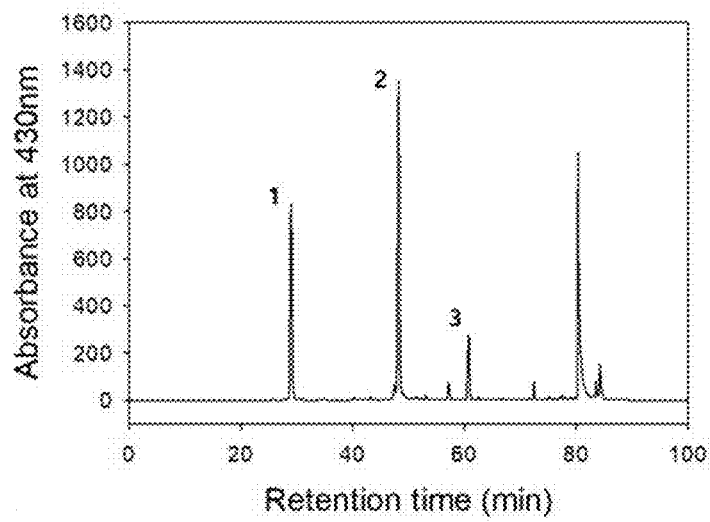
Figure 5B:
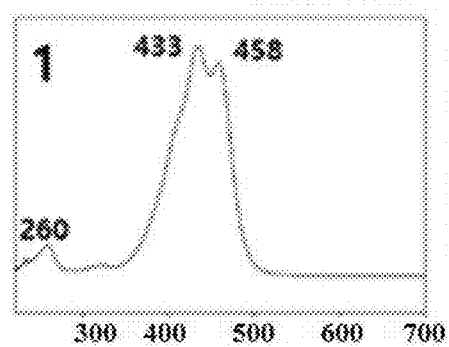
Figure 5B:
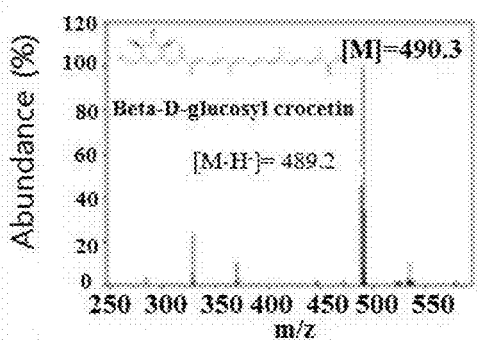
Figure 5B:
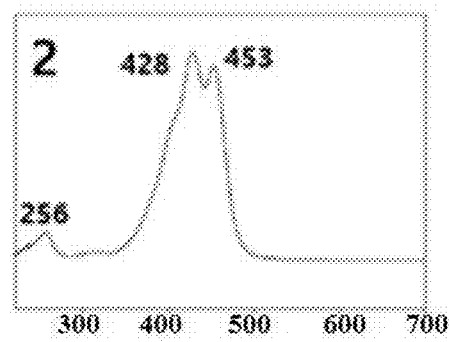
Figure 5B:
Figure 5B:
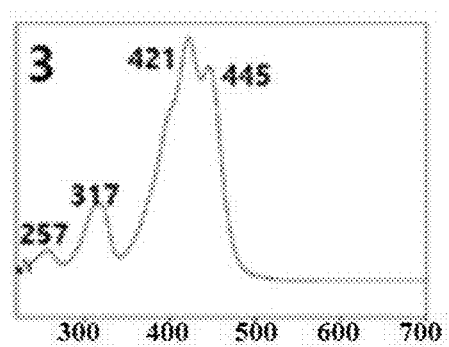
Figure 5B:

As a result, as can be confirmed in FIGS. 5A-5B, it was confirmed that a peak (peak-1) representing crocin-5 was observed. In addition, as a result of analyzing the mass spectrum, it was confirmed that a high concentration of crocin-5 was produced. Through this, recombinant microorganisms in which a gene (CsCCD2) encoding crocetin dialdehyde biosynthesis enzyme, a gene (aldH_7942) encoding crocetin biosynthesis enzyme, and a gene (UGT-1) encoding crocin biosynthesis enzyme into strains in which the MEP metabolic pathway and zeaxanthin biosynthesis pathway were advanced could produce crocin-5 with high efficiency.

2-4. Confirmation of Crocin-3 Biosynthesis

As explained in Example 1, the biosynthesis of crocin-3 of the recombinant microorganism transformed with the gene (CsCCD2) encoding the crocetin dialdehyde biosynthesis enzyme, the gene (aldH_7942) encoding the crocetin biosynthesis enzyme, and the gene (UGT-1) encoding the crocin biosynthesis enzyme into strains which the MEP metabolic pathway and zeaxanthin biosynthesis pathway were inserted was confirmed.

Specifically, the recombinant microorganism was incubated at 250 rpm under aerobic conditions in a 100 ml TB medium using a 500 ml flask. In the case of the incubation temperature, the incubation was carried out at 30° C., and when OD600 became between 0.7 and 1.0, the temperature was converted into 20° C., and then the incubation was continued. As the medium composition, 50 µg/ml of chloramphenicol, 100 µg/ml of ampicillin and 50 µg/ml of kanamycin were all added to a TB medium containing 5 g/L of glycerol as a carbon source.

100 ml of medium with the cultured recombinant microorganisms for extraction and separation of crocin-3 was all taken, and centrifuged at 4000 rpm for 20 minutes, and the cells and the supernatant were separated and were all taken. Ethyl acetate and 5N NaCl were treated with the same volume in the obtained supernatant, and then reacted for 48 hours in a dark place indoors. Then, the ethyl acetate layer was taken. Water was removed using $MgSO_4$. The extracted solution was added to 100-200 µl of ethyl acetate and used for later analysis.

Figure 6A:
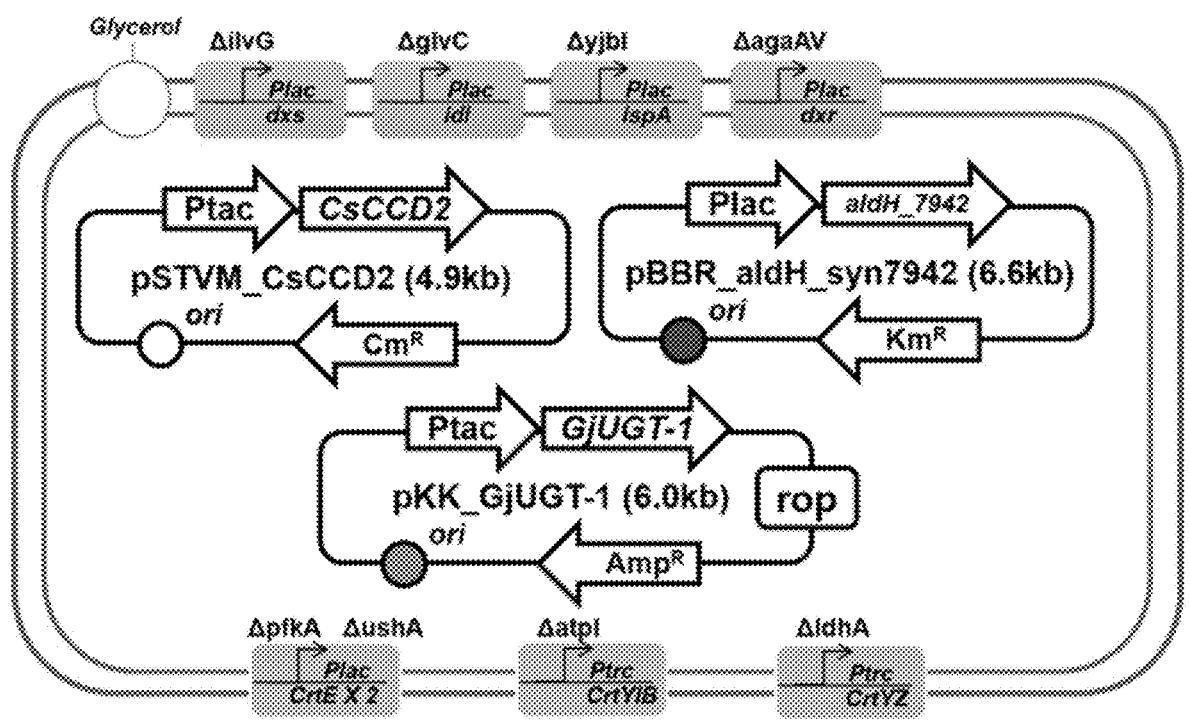
FIGS. 6A and 6B illustrate crocin-3 biosynthetic metabolic pathway constructed in *E. coli* and a schematic diagram of transforming UGT-1 gene into a strain that can biosynthesize crocetin in order to biosynthesize crocin (FIG. 6A), and an HPLC spectrum analysis result (FIG. 6B).
Figure 6B:
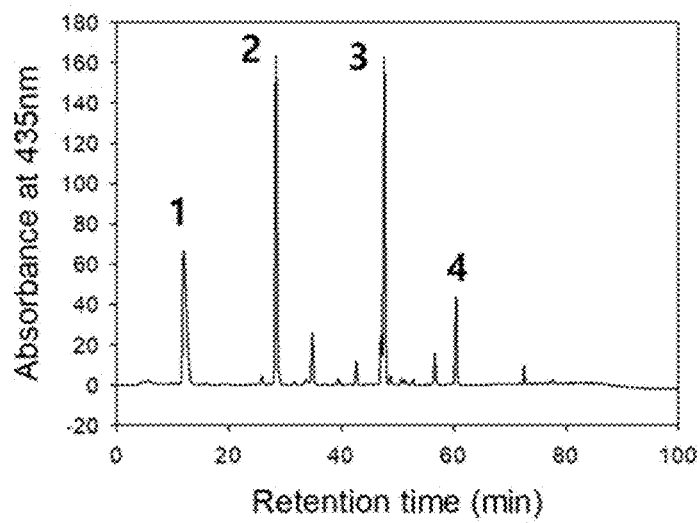
Figure 6B:
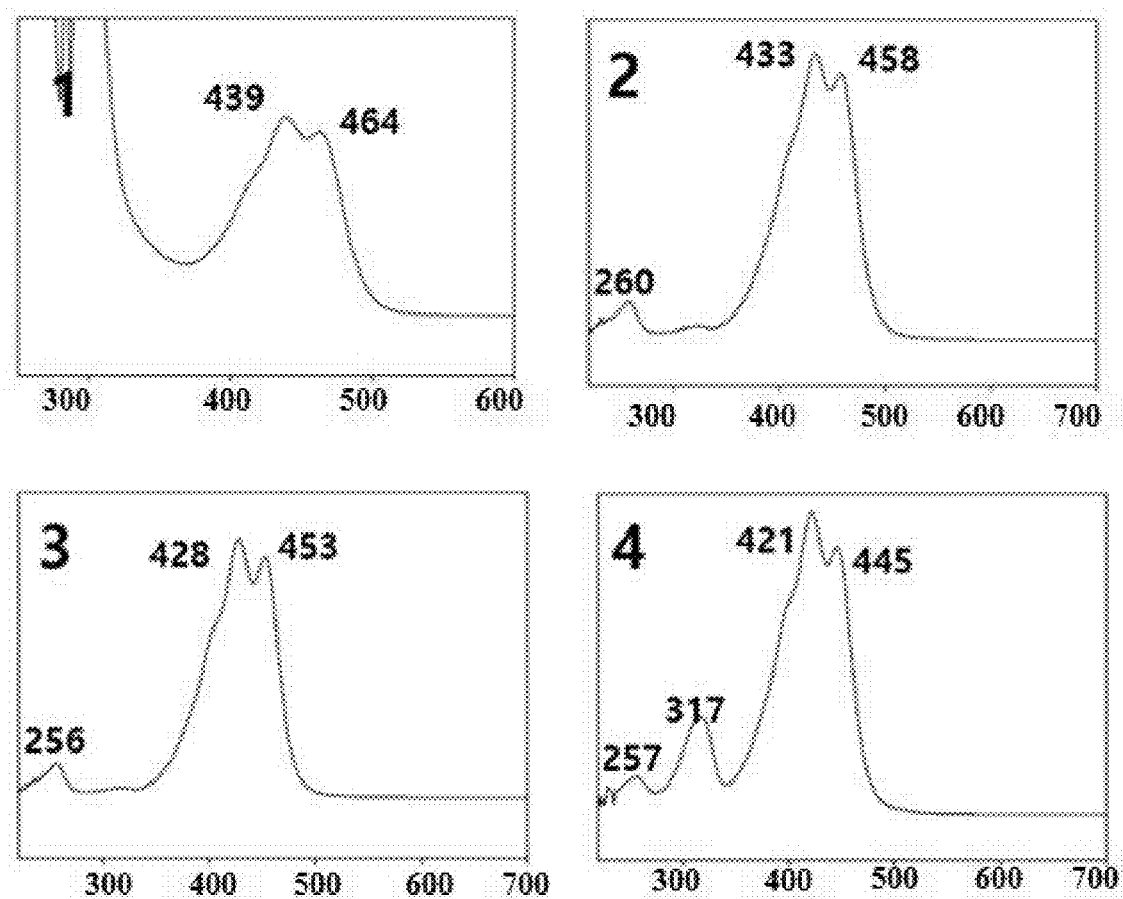

As a result, as can be confirmed in FIGS. 6A-6B, it was confirmed that a peak representing crocin-3 (peak-1) and a peak representing crocin-5 (peak-2) were observed. Through this, recombinant microorganisms in which a gene (CsCCD2) encoding crocetin dialdehyde biosynthesis enzyme, a gene (aldH_7942) encoding crocetin biosynthesis enzyme, and a gene (UGT-1) encoding crocin biosynthesis enzyme were introduced into strains in which the MEP metabolic pathway and zeaxanthin biosynthesis pathway were advanced could also produce crocin-3 with high efficiency.

<Example 3> Comparison of Crocin Production According to Origin of Introduced Genes In order to confirm the change in the efficiency of crocin biosynthesis according to the origin of the gene introduced into the recombinant microorganism, the production amount of crocetin of the case of introducing a gene (aldH_7942) encoding crocetin biosynthesis enzyme derived from *Synechococcus elongatus* PCC 7942 and the case of introducing a gene encoding a crocetin biosynthesis enzyme aldH 6803 derived from *Synechococcus elongatus* PCC 6803 was compared.

As a result, as can be confirmed in Table 3 below, when the aldH 7942 gene of the present disclosure was introduced, it was confirmed that the production amount of crocetin increased by about 1.5 times. Through this, it was confirmed that the efficiency of biosynthesis of crocetin and crocin may vary significantly depending on the origin of the gene introduced into the recombinant microorganism for producing crocin.

TABLE 3

| ZEA-1_pSTVM_CsCCD2 + pBBR_aldHS | Crocetin (µg/L) | µg/DCW | µg/Glycerol |
|---|---|---|---|
| aldH6803 | 698.66 ± 37.25 | 129.4 ± 10.45 | 67.23 ± 3.72 |
| aldH7942 | 986.55 ± 41.65 | 196.35 ± 1.36 | 98.65 ± 4.17 |

In the above results, it was confirmed that the carotenoid cleavage enzyme gene (CsCCD2), the crocetin biosynthesis enzyme gene (aldH_7942) and the crocin biosynthesis enzyme gene (UGT-1) were introduced into strains in which the MEP metabolic pathway and zeaxanthin metabolic pathway were advanced to produce a recombinant microorganism for producing crocin (FIGS. 1A and 1B). As the three genes were sequentially introduced, the recombinant microorganisms were able to biosynthesize crocetin dialdehyde, crocetin and crocin, respectively (FIGS. 2A, 2B, 3A-3C, 4A, 4B, 5A, 5B, 6A and 6B). Furthermore, it was confirmed that the biosynthetic efficiency of crocetin and crocin may vary significantly depending on the three genes derived (Table 3).

From the above description, those skilled in the art will appreciate that the present disclosure can be implemented in other specific forms without changing the technical spirit or essential features. In this regard, it should be understood that the embodiments described above are exemplary in all respects and not limiting. The scope of the present disclosure should be construed that all changes or modifications derived from the meaning and scope of the following claims and equivalent concepts rather than the detailed description are included in the scope of the present disclosure.

What is claimed is:

1. A method for producing crocin, comprising culturing a recombinant microorganism,
   wherein the recombinant microorganism is prepared by introducing
   a gene encoding carotenoid cleavage dioxygenase 2 (CCD2) comprising the amino acid sequence of SEQ ID NO: 1,
   a gene encoding crocetin aldehyde dehydrogenase (aldH) comprising the amino acid sequence of SEQ ID NO: 2, and
   a gene encoding UDP-glycosyltransferase (UGT) comprising the amino acid sequence of SEQ ID NO: 3, into a microorganism which produces zeaxanthin.

2. The method of claim 1, further comprising recovering crocin from the cultured recombinant microorganism or its culture.

3. The method of claim 1, wherein the microorganism is from the genus *Saccharomyces* or the genus *Escherichia*.

4. The method of claim 3, wherein the microorganism of the genus *Saccharomyces* is *Saccharomyces cerevisiae*.

5. The method of claim 3, wherein the microorganism of the genus *Escherichia* is *Escherichia coli*.

* * * * *

SEQUENCE LISTING

<160> NUMBER OF SEQ ID NOS: 16

<210> SEQ ID NO 1
<211> LENGTH: 562
<212> TYPE: PRT
<213> ORGANISM: Crocus sativus

<400> SEQUENCE: 1

Met Ala Asn Lys Glu Glu Ala Glu Lys Arg Lys Lys Pro Lys Pro
1               5                   10                  15

Leu Lys Val Leu Ile Thr Lys Val Asp Pro Lys Pro Arg Lys Gly Met
            20                  25                  30

Ala Ser Val Ala Val Asp Leu Leu Glu Lys Ala Phe Val Tyr Leu Leu
        35                  40                  45

Ser Gly Asn Ser Ala Ala Asp Arg Ser Ser Ser Gly Arg Arg Arg
    50                  55                  60

Arg Lys Glu His Tyr Tyr Leu Ser Gly Asn Tyr Ala Pro Val Gly His
65              70                  75                  80

Glu Thr Pro Pro Ser Asp His Leu Pro Ile His Gly Ser Leu Pro Glu
                85                  90                  95

Cys Leu Asn Gly Val Phe Leu Arg Val Gly Pro Asn Pro Lys Phe Ala
            100                 105                 110

Pro Val Ala Gly Tyr Asn Trp Val Asp Gly Asp Gly Met Ile His Gly
        115                 120                 125

Leu Arg Ile Lys Asp Gly Lys Ala Thr Tyr Leu Ser Arg Tyr Ile Lys
    130                 135                 140

Thr Ser Arg Phe Lys Gln Glu Glu Tyr Phe Gly Arg Ala Lys Phe Met
145             150                 155                 160

Lys Ile Gly Asp Leu Arg Gly Leu Leu Gly Phe Phe Thr Ile Leu Ile
            165                 170                 175

Leu Val Leu Arg Thr Thr Leu Lys Val Ile Asp Ile Ser Tyr Gly Arg
        180                 185                 190

Gly Thr Gly Asn Thr Ala Leu Val Tyr His Asn Gly Leu Leu Leu Ala
    195                 200                 205

Leu Ser Glu Glu Asp Lys Pro Tyr Val Lys Val Leu Glu Asp Gly
210                 215                 220

Asp Leu Gln Thr Leu Gly Ile Leu Asp Tyr Asp Lys Lys Leu Ser His
225                 230                 235                 240

Pro Phe Thr Ala His Pro Lys Ile Asp Pro Leu Thr Asp Glu Met Phe
            245                 250                 255

Thr Phe Gly Tyr Ser Ile Ser Pro Pro Tyr Leu Thr Tyr Arg Val Ile
        260                 265                 270

Ser Lys Asp Gly Val Met Gln Asp Pro Val Gln Ile Ser Ile Thr Ser
    275                 280                 285

Pro Thr Ile Met His Asp Phe Ala Ile Thr Glu Asn Tyr Ala Ile Phe
290                 295                 300

Met Asp Leu Pro Leu Tyr Phe Gln Pro Glu Glu Met Val Lys Gly Lys
305                 310                 315                 320

Phe Val Ser Ser Phe His Pro Thr Lys Arg Ala Arg Ile Gly Val Leu
            325                 330                 335

Pro Arg Tyr Ala Lys Asp Glu His Pro Ile Arg Trp Phe Asp Leu Pro
        340                 345                 350

Ser Cys Phe Met Thr His Asn Ala Asn Ala Trp Glu Glu Asn Asp Glu
    355                 360                 365

Val Val Leu Phe Thr Cys Arg Leu Glu Ser Pro Asp Leu Asp Met Leu
370                 375                 380

Ser Gly Pro Ala Glu Glu Ile Gly Asn Ser Lys Ser Glu Leu Tyr
385                 390                 395                 400

-continued

Glu Met Arg Phe Asn Leu Lys Thr Gly Ile Thr Ser Gln Lys Gln Leu
                405                 410                 415

Ser Val Pro Ser Val Asp Phe Pro Arg Ile Asn Gln Ser Tyr Thr Gly
            420                 425                 430

Arg Lys Gln Gln Tyr Val Tyr Cys Thr Leu Gly Asn Thr Lys Ile Lys
        435                 440                 445

Gly Ile Val Lys Phe Asp Leu Gln Ile Glu Pro Glu Ala Gly Lys Thr
    450                 455                 460

Met Leu Glu Val Gly Gly Asn Val Gln Gly Ile Phe Glu Leu Gly Pro
465                 470                 475                 480

Arg Arg Tyr Gly Ser Glu Ala Ile Phe Val Pro Cys Gln Pro Gly Ile
                485                 490                 495

Lys Ser Asp Glu Asp Asp Gly Tyr Leu Ile Phe Phe Val His Asp Glu
            500                 505                 510

Asn Asn Gly Lys Ser Glu Val Asn Val Ile Asp Ala Lys Thr Met Ser
        515                 520                 525

Ala Glu Pro Val Ala Val Glu Leu Pro Ser Arg Val Pro Tyr Gly
    530                 535                 540

Phe His Ala Leu Phe Leu Asn Glu Glu Glu Leu Gln Lys His Gln Ala
545                 550                 555                 560

Glu Thr

<210> SEQ ID NO 2
<211> LENGTH: 459
<212> TYPE: PRT
<213> ORGANISM: Synechococcus elongatus

<400> SEQUENCE: 2

Met Thr Ala Val Val Leu Pro Ala Ala Ala Glu Thr Leu Ala Ala Leu
1               5                   10                  15

Gln Ala Thr Phe Asp Arg Gly Asp Thr Arg Thr Leu Ala Phe Arg Leu
            20                  25                  30

Ala Arg Leu Gln Asp Leu Ala Lys Leu Val Ala Asp Asn Glu Ala Glu
        35                  40                  45

Leu Leu Gln Ala Leu Ala Ser Asp Leu Arg Lys Pro Ala Leu Glu Ala
    50                  55                  60

Tyr Ala Ser Glu Ile Tyr Phe Val Arg Asp Gln Ile Lys Leu Thr Cys
65                  70                  75                  80

Lys His Leu Arg Arg Trp Met Gln Pro Glu Lys Gln Ser Ile Ser Leu
                85                  90                  95

Met Gln Gln Pro Gly Gln Ala Tyr Arg Gln Ala Glu Pro Leu Gly Val
            100                 105                 110

Val Leu Ile Ile Gly Pro Trp Asn Tyr Pro Phe Gln Leu Leu Ile Thr
        115                 120                 125

Pro Leu Ile Gly Ala Ile Ala Ala Gly Asn Cys Ala Val Leu Lys Pro
    130                 135                 140

Ser Glu Leu Ala Pro Ala Thr Ser Ser Leu Ile Gln Arg Leu Ile Ser
145                 150                 155                 160

Asp Arg Phe Asp Pro Asp Tyr Ile Arg Val Leu Glu Gly Asp Ala Ser
                165                 170                 175

Val Ser Gln Ala Leu Ile Thr Gln Pro Phe Asp His Ile Phe Phe Thr
            180                 185                 190

Gly Gly Thr Ala Ile Gly Arg Lys Val Met Ala Ala Ala Glu Asn
        195                 200                 205

```
Leu Thr Pro Val Thr Leu Glu Leu Gly Gly Lys Ser Pro Cys Ile Val
    210                 215                 220

Asp Thr Asp Ile Asp Leu Asp Val Ala Ala Arg Arg Ile Ala Trp Gly
225                 230                 235                 240

Lys Phe Phe Asn Ala Gly Gln Thr Cys Ile Ala Pro Asp Tyr Leu Leu
                245                 250                 255

Val Gln Arg Thr Val Ala Glu Pro Phe Ile Glu Ala Leu Ile Asp Asn
            260                 265                 270

Ile Gln Gln Phe Tyr Gly Glu Asp Pro Gln Gln Ser Ala Asp Tyr Ala
        275                 280                 285

Arg Ile Val Ser Asp Arg His Trp Gln Arg Leu Asn Ser Leu Leu Val
    290                 295                 300

Asp Gly Thr Ile Arg His Gly Gln Val Asp Arg Ser Asp Arg Tyr
305                 310                 315                 320

Ile Ala Pro Thr Leu Ile Thr Asp Val Asn Trp Arg Asp Pro Ile Leu
                325                 330                 335

Gln Glu Glu Ile Phe Gly Pro Leu Leu Pro Ile Leu Ile Tyr Asp Gln
            340                 345                 350

Leu Asp Glu Ala Ile Ala Gln Ile Arg Ala Gln Pro Lys Pro Leu Ala
        355                 360                 365

Leu Tyr Leu Phe Ser Arg Asp Arg Gln Val Gln Glu Arg Val Leu Ala
    370                 375                 380

Glu Thr Ser Ala Gly Ser Val Cys Leu Asn Asp Thr Ile Leu Gln Val
385                 390                 395                 400

Gly Val Pro Asp Ala Ala Phe Gly Gly Val Gly Pro Ser Gly Met Gly
                405                 410                 415

Gly Tyr His Gly Lys Ala Ser Phe Glu Thr Phe Ser His Tyr Lys Leu
            420                 425                 430

Val Leu Lys Arg Pro Phe Trp Leu Asp Leu Ala Leu Arg Tyr Pro Pro
        435                 440                 445

Tyr Gly Asp Lys Ile Asn Leu Phe Arg Lys Leu
    450                 455

<210> SEQ ID NO 3
<211> LENGTH: 474
<212> TYPE: PRT
<213> ORGANISM: Gardenia jasminoides

<400> SEQUENCE: 3

Met Val Gln Gln Arg His Val Leu Leu Ile Thr Tyr Pro Ala Gln Gly
1               5                   10                  15

His Ile Asn Pro Ala Leu Gln Phe Ala Gln Arg Leu Leu Arg Met Gly
                20                  25                  30

Ile Gln Val Thr Leu Ala Thr Ser Val Tyr Ala Leu Ser Arg Met Lys
            35                  40                  45

Lys Ser Ser Gly Ser Thr Pro Lys Gly Leu Thr Phe Ala Thr Phe Ser
        50                  55                  60

Asp Gly Tyr Asp Gly Phe Arg Pro Lys Gly Val Asp His Thr Glu
65                  70                  75                  80

Tyr Met Ser Ser Leu Ala Lys Gln Gly Ser Asn Thr Leu Arg Asn Val
                85                  90                  95

Ile Asn Thr Ser Ala Asp Gln Gly Cys Pro Val Thr Cys Leu Val Tyr
            100                 105                 110
```

Thr Leu Leu Leu Pro Trp Ala Ala Thr Val Ala Arg Glu Cys His Ile
            115                 120                 125

Pro Ser Ala Leu Leu Trp Ile Gln Pro Val Ala Val Met Asp Ile Tyr
        130                 135                 140

Tyr Tyr Tyr Phe Arg Gly Tyr Glu Asp Val Lys Asn Asn Ser Asn
145                 150                 155                 160

Asp Pro Thr Trp Ser Ile Gln Phe Pro Gly Leu Pro Ser Met Lys Ala
                165                 170                 175

Lys Asp Leu Pro Ser Phe Ile Leu Pro Ser Asp Asn Ile Tyr Ser
            180                 185                 190

Phe Ala Leu Pro Thr Phe Lys Lys Gln Leu Glu Thr Leu Asp Glu Glu
        195                 200                 205

Glu Arg Pro Lys Val Leu Val Asn Thr Phe Asp Ala Leu Glu Pro Gln
    210                 215                 220

Ala Leu Lys Ala Ile Glu Ser Tyr Asn Leu Ile Ala Ile Gly Pro Leu
225                 230                 235                 240

Thr Pro Ser Ala Phe Leu Asp Gly Lys Asp Pro Ser Glu Thr Ser Phe
                245                 250                 255

Ser Gly Asp Leu Phe Gln Lys Ser Lys Asp Tyr Lys Glu Trp Leu Asn
            260                 265                 270

Ser Arg Pro Ala Gly Ser Val Tyr Val Ser Phe Gly Ser Leu Leu
        275                 280                 285

Thr Leu Pro Lys Gln Gln Met Glu Glu Ile Ala Arg Gly Leu Leu Lys
    290                 295                 300

Ser Gly Arg Pro Phe Leu Trp Val Ile Arg Ala Lys Glu Asn Gly Glu
305                 310                 315                 320

Glu Glu Lys Glu Glu Asp Arg Leu Ile Cys Met Glu Glu Leu Glu Glu
                325                 330                 335

Gln Gly Met Ile Val Pro Trp Cys Ser Gln Ile Glu Val Leu Thr His
            340                 345                 350

Pro Ser Leu Gly Cys Phe Val Thr His Cys Gly Trp Asn Ser Thr Leu
        355                 360                 365

Glu Thr Leu Val Cys Gly Val Pro Val Val Ala Phe Pro His Trp Thr
    370                 375                 380

Asp Gln Gly Thr Asn Ala Lys Leu Ile Glu Asp Val Trp Glu Thr Gly
385                 390                 395                 400

Val Arg Val Val Pro Asn Glu Asp Gly Thr Val Glu Ser Asp Glu Ile
                405                 410                 415

Lys Arg Cys Ile Glu Thr Val Met Asp Asp Gly Glu Lys Gly Val Glu
            420                 425                 430

Leu Lys Arg Asn Ala Lys Lys Trp Lys Glu Leu Ala Arg Glu Ala Met
        435                 440                 445

Gln Glu Asp Gly Ser Ser Asp Lys Asn Leu Lys Ala Phe Val Glu Asp
    450                 455                 460

Ala Gly Lys Gly Tyr Gln Ala Glu Ser Asn
465                 470

<210> SEQ ID NO 4
<211> LENGTH: 1689
<212> TYPE: DNA
<213> ORGANISM: Crocus sativus

<400> SEQUENCE: 4

```
atggcgaaca aagaagaggc ggaaaaacgc aagaaaaaac cgaagccgct gaaggtgctg      60
attaccaaag ttgacccgaa accgcgcaag ggtatggcga gcgttgcggt ggatctgctg     120
gaaaaagcgt tcgtttatct gctgagcggc aacagcgcgg cggatcgtag cagcagcagc     180
ggtcgtcgtc gtcgtaaaga gcactactat ctgagcggta actacgcgcc ggttggtcac     240
gaaaccccgc cgagcgatca cctgccgatc acggtagcc tgccgagtg cctgaacggt      300
gtgtttctgc gtgtgggtcc gaacccgaag ttcgcgccgg tggcgggtta caactgggtt     360
gacggtgacg gcatgattca cggtctgcgt atcaaagacg gtaaagcgac ctatctgagc     420
cgttacatca agaccagccg tttcaagcaa gaggaatact cggtcgtgc gaaattcatg      480
aagattggcg atctgcgtgg tctgctgggc ttctttacca ttctgatcct ggtgctgcgt     540
accaccctga aggtgatcga tattagctat ggtcgtggca ccggtaacac cgcgctggtg     600
tatcacaacg tctgctgct ggcgctgagc gaggaagaca gccgtatgt tgtgaaagtt      660
ctggaggatg gtgacctgca aaccctgggt atcctggatt cgacaagaa actgagccac     720
ccgttcaccg cgcaccccgaa gattgacccg ctgaccgacg aaatgtttac cttcggctat     780
agcattagcc cgccgtatct gacctatcgt gtgattagca agacggcgt tatgcaggac     840
ccggttcaga tcagcattac cagcccgacc attatgcacg attcgcgat taccgaaaac     900
tatgcgatct tcatggatct gccgctgtac tttcagccgg aagagatggt gaagggtaaa     960
ttcgtgagca gcttccaccc gaccaaacgt gcgcgtattg gtgttctgcc gcgttacgcg    1020
aaagatgaac accgattcg ttggtttgac ctgccgagct gcttcatgac ccacaacgcg    1080
aacgcgtggg aggaaaacga cgaggttgtg ctgttcacct gccgtctgga gagcccggat    1140
ctggacatgc tgagcggccc ggcggaagaa gagattggca cagcaagag cgagctgtat    1200
gaaatgcgtt tcaacctgaa gaccggtatc accagccaga agcagctgag cgttccgagc    1260
gttgactttc gcgtatcaa ccagagctac accggtcgta agcaacagta tgtgtactgc    1320
accctgggta acaccaagat taaaggcatc gtgaagttcg atctgcaaat tgagccggaa    1380
gcgggtaaaa ccatgctgga agttggtggc aacgttcaag gcatttttga actgggtccg    1440
cgtcgttacg gtagcgaagc gatcttcgtt ccgtgccaac cgggtattaa agcgatgaa    1500
gacgatggtt acctgatttt cttttgtgcac gacgaaaaca acgtaaaag cgaagttaac    1560
gtgattgatg cgaaaaccat gagcgcggag ccggttgcgg tggttgagct gccgagccgt    1620
gtgccgtatg gtttccacgc gctgttcctg aatgaagaag agctgcaaaa gcatcaagcg    1680
gagacctaa                                                            1689
```

<210> SEQ ID NO 5
<211> LENGTH: 1380
<212> TYPE: DNA
<213> ORGANISM: Synechococcus elongatus

<400> SEQUENCE: 5

```
atgactgctg tcgttctccc tgctgccgct gaaacgctgg ctgctttaca agcaaccttt      60
gatcggggg atacacgcac gctcgccttc cgactggcgc gattacagga tctggccaag     120
ctagttgctg acaatgaagc ggagctattg caagccttgg cgtcagacct ccgcaaacca     180
gcactggaag cctacgccag tgagatttat ttcgtgcgcg accaaatcaa actgaccctgc    240
aagcatctgc ggcgctggat gcaacccgag aagcagtcga tttccttgat gcagcagcct     300
```

| | |
|---|---|
| ggccaggcct atcgccaagc agaaccgctc ggagtcgtgc tgatcattgg ccctggaac | 360 |
| tatcccttc agctgctcat cacgccgttg attgggcga tcgcggcggg aaattgtgcc | 420 |
| gtactcaaac catcggaact ggctcccgcg acttccagcc tgattcagcg actgatcagc | 480 |
| gatcgctttg accctgatta catccgcgtt ttagaaggcg atgctagcgt tagccaagcc | 540 |
| ctgattactc agcccttcga tcacatcttc ttcactggcg gcacggcgat cgggcgaaaa | 600 |
| gtgatggctg ctgcggccga aaacctgacg cccgtcaccc tcgagttggg cggtaagtca | 660 |
| ccctgcattg ttgataccga tatcgacctc gatgtggccg cccgtcgcat cgcctggggc | 720 |
| aaattcttca cgccggtca aacctgcatt gcgcctgact atttgttggt gcaacgcacg | 780 |
| gtcgcagagc cgttcattga agcgctgatc gacaacatcc agcagttcta tggcgaggat | 840 |
| ccgcaacaga gtgctgacta cgcccgcatt gtcagcgatc gccactggca aaggctaaat | 900 |
| agcctgttgg ttgatggcac gattcgccat ggtggtcagg tggataggag cgatcgctac | 960 |
| atcgcaccga cttaattac ggacgtcaac tggcgcgatc ccatcctgca agaggagatt | 1020 |
| tttgggcccc tcttgccgat tttgatttac gaccaattgg atgaggcgat cgcccaaatt | 1080 |
| cgtgcccagc caagcccct cgcgctctat ctattcagcc gcgatcgcca agtgcaagag | 1140 |
| cgcgtcctag cggaaaccag cgccggtagc gtctgcctca acgacacgat cctgcaggtc | 1200 |
| ggcgtccccg atgctgcttt tggtggggtc ggcccagcg gcatgggcgg ctatcacggc | 1260 |
| aaagccagtt tcgaaacctt cagtcactac aagctggtgc tcaagcgacc gttttggctc | 1320 |
| gatctggccc tgcgctatcc gccctacggc gacaagatca acctcttccg caagctctag | 1380 |

<210> SEQ ID NO 6
<211> LENGTH: 1425
<212> TYPE: DNA
<213> ORGANISM: Gardenia jasminoides

<400> SEQUENCE: 6

| | |
|---|---|
| atggttcagc agcgtcacgt tttgttgatt acctatccag cacagggtca cattaaccca | 60 |
| gcgttgcagt tcgcacagag attgttgcgt atgggtattc aagttaccct ggcgaccagc | 120 |
| gtgtacgctc tgagccgtat gaaaaagagc agcggtagca ccccgaaagg tctgaccttt | 180 |
| gcaaccttca gcgatggtta cgatgacggt tttcgtccga aaggtgttga ccataccgaa | 240 |
| tatatgagca gcctggcgaa gcaaggtagc aataccctgc gtaatgtgat caacaccagc | 300 |
| gctgatcagg gttgcccggt tacctgtttg gtgtataccc tgttgctgcc atgggctgct | 360 |
| accgttgcac gtgaatgcca cattccgagc gcgctgctgt ggatccaacc ggttgctgtg | 420 |
| atggatatct actattacta tttccgtggt tatgaagatg acgttaagaa taacagcaat | 480 |
| gacccgacct ggagcatcca gtttccgggt ctgccgagca tgaaagctaa ggatctgccg | 540 |
| agcttcattc tgccgagcag cgacaacatc tacagctttg cactgccgac cttcaaaaag | 600 |
| caactggaaa ccctggatga agaagaacgt ccgaaagttc tggtgaatac ctttgacgcg | 660 |
| ctggaaccgc aggcactgaa ggcgattgaa agctataacc tgattgcaat ggtccactg | 720 |
| accccgagcg cgttcctgga tggtaaagac ccgagcgaaa ccagctttag cggtgacctg | 780 |
| tttcagaaaa gcaaggacta caaggaatgg ctgaatagcc gtccggctgg tagcgttgtg | 840 |
| tatgttagct ttggtagcct gctgaccctg ccgaaacaac agatggaaga aattgcacgt | 900 |
| ggtctgctga gagcggtcg tccgttcctg tgggttattc gtgcgaaaga aaacggtgaa | 960 |
| gaagaaaagg aagaagatcg tctgatttgc atggaagaac tggaagaaca gggtatgatt | 1020 |
| gttccgtggt gtagccagat cgaagtgctg acccatccga gcctgggttg ctttgttacc | 1080 |

```
cactgtggtt ggaatagcac cctggaaacc ctggtttgcg gtgtgccggt tgtggctttc   1140
ccgcattgga ccgatcaagg taccaatgca aaactgatcg aagacgtttg ggaaccggt    1200 gtgcgtgttg tgccgaacga agatggtacc gttgaaagcg acgaaattaa acgttgtatc   1260
gaaaccgtta tggatgacgg tgaaaaaggt gtggaactga agcgtaacgc gaaaaagtgg   1320
aaggaactgg ctcgtgaagc aatgcaggaa gatggtagca gcgacaaaaa cctgaaagcg   1380
ttcgtggagg atgcgggcaa gggctatcaa gcggagagca actaa              1425
```

<210> SEQ ID NO 7
<211> LENGTH: 27
<212> TYPE: DNA
<213> ORGANISM: Artificial Sequence
<220> FEATURE:
<223> OTHER INFORMATION: Synthetic CsCCD2 forward primer

<400> SEQUENCE: 7

```
cggaattcat ggcgaacaaa gaagagg                                      27
```

<210> SEQ ID NO 8
<211> LENGTH: 28
<212> TYPE: DNA
<213> ORGANISM: Artificial Sequence
<220> FEATURE:
<223> OTHER INFORMATION: Synthetic CsCCD2 reverse primer

<400> SEQUENCE: 8

```
cccaagcttt taggtctccg cttgatgc                                     28
```

<210> SEQ ID NO 9
<211> LENGTH: 41
<212> TYPE: DNA
<213> ORGANISM: Artificial Sequence
<220> FEATURE:
<223> OTHER INFORMATION: Synthetic aldH_7942 forward primer

<400> SEQUENCE: 9

```
gctctagaag gaggattaca aaatgactgc tgtcgttctc c                      41
```

<210> SEQ ID NO 10
<211> LENGTH: 26
<212> TYPE: DNA
<213> ORGANISM: Artificial Sequence
<220> FEATURE:
<223> OTHER INFORMATION: Synthetic aldH_7942 reverse primer

<400> SEQUENCE: 10

```
cggaattcct agagcttgcg gaagag                                       26
```

<210> SEQ ID NO 11
<211> LENGTH: 26
<212> TYPE: DNA
<213> ORGANISM: Artificial Sequence
<220> FEATURE:
<223> OTHER INFORMATION: Synthetic sub CCD2 forward primer

<400> SEQUENCE: 11

```
ggaagatctg ctgtgcaggt cgtaaa                                       26
```

<210> SEQ ID NO 12
<211> LENGTH: 33
<212> TYPE: DNA
<213> ORGANISM: Artificial Sequence

```
<220> FEATURE:
<223> OTHER INFORMATION: Synthetic sub CCD2 reverse primer

<400> SEQUENCE: 12
ataagaatgc ggccgcgaaa cgcaaaaagg cca                          33

<210> SEQ ID NO 13
<211> LENGTH: 20
<212> TYPE: DNA
<213> ORGANISM: Artificial Sequence
<220> FEATURE:
<223> OTHER INFORMATION: Synthetic sub aldH_7942 forward primer

<400> SEQUENCE: 13
gtcgacccga ctggaaagcg                                         20

<210> SEQ ID NO 14
<211> LENGTH: 26
<212> TYPE: DNA
<213> ORGANISM: Artificial Sequence
<220> FEATURE:
<223> OTHER INFORMATION: Synthetic sub aldH_7942 reverse primer

<400> SEQUENCE: 14
cggaattcct agagcttgcg gaagag                                  26

<210> SEQ ID NO 15
<211> LENGTH: 28
<212> TYPE: DNA
<213> ORGANISM: Artificial Sequence
<220> FEATURE:
<223> OTHER INFORMATION: Synthetic UGT-1 forward primer

<400> SEQUENCE: 15
cggaattcat ggttcagcag cgtcacgt                                28

<210> SEQ ID NO 16
<211> LENGTH: 28
<212> TYPE: DNA
<213> ORGANISM: Artificial Sequence
<220> FEATURE:
<223> OTHER INFORMATION: Synthetic UGT-1 reverse primer

<400> SEQUENCE: 16
aactgcagtt agttgctctc cgcttgat                                28
```